(12) United States Patent
Schacht et al.

(10) Patent No.: US 10,315,146 B2
(45) Date of Patent: Jun. 11, 2019

(54) FILTER MEDIUM FOR DEACTIVATING ALLERGENS

(71) Applicant: Carl Freudenberg KG, Weinheim (DE)

(72) Inventors: Heiko Schacht, Weinheim (DE); Uwe Haefner, Kehl (DE); Oliver Staudenmayer, Weinheim (DE)

(73) Assignee: CARL FREUDENBERG KG, Weinheim (DE)

( * ) Notice: Subject to any disclaimer, the term of this patent is extended or adjusted under 35 U.S.C. 154(b) by 309 days.

(21) Appl. No.: 15/336,844

(22) Filed: Oct. 28, 2016

(65) Prior Publication Data

US 2017/0120178 A1    May 4, 2017

(30) Foreign Application Priority Data

Nov. 2, 2015 (EP) .................................. 15192601

(51) Int. Cl.
| | | |
|---|---|---|
| *B01D 46/00* | (2006.01) | |
| *B01D 24/00* | (2006.01) | |
| *B01D 39/16* | (2006.01) | |
| *A61L 9/00* | (2006.01) | |
| *B01D 46/52* | (2006.01) | |

(52) U.S. Cl.
CPC .............. *B01D 46/0028* (2013.01); *A61L 9/00* (2013.01); *B01D 24/00* (2013.01); *B01D 24/007* (2013.01); *B01D 39/1623* (2013.01); *B01D 46/0036* (2013.01); *B01D 46/0038* (2013.01); *B01D 46/521* (2013.01); *A61L 2209/14* (2013.01); *A61L 2209/22* (2013.01); *B01D 2239/0407* (2013.01); *B01D 2239/0442* (2013.01); *B01D 2239/065* (2013.01); *B01D 2279/40* (2013.01); *B01D 2279/50* (2013.01)

(58) Field of Classification Search
CPC .............................. B01D 24/00; B01D 24/007
USPC ..................................................... 55/482, 486
See application file for complete search history.

(56) References Cited

U.S. PATENT DOCUMENTS

| | | | | |
|---|---|---|---|---|
| 6,524,360 | B2 * | 2/2003 | Cox .................... | B01D 39/1623 |
| | | | | 264/169 |
| 2013/0183879 | A1 | 7/2013 | Lee et al. | |

FOREIGN PATENT DOCUMENTS

| | | | |
|---|---|---|---|
| EP | 2879776 A1 | 6/2015 | |
| JP | 2002058729 A * | 2/2002 | ............... A61L 9/16 |
| JP | 2006206763 A | 8/2006 | |
| JP | 2007007615 A | 1/2007 | |
| KR | 1020120035507 A | 10/2010 | |
| WO | WO 2014019660 A1 | 2/2014 | |

* cited by examiner

*Primary Examiner* — Robert A Hopkins
(74) *Attorney, Agent, or Firm* — Leydig, Voit & Mayer, Ltd.

(57) ABSTRACT

Filter medium, comprising at least one acid-functionalized layer, characterized in that the acid-functionalized layer has a first acid with a pks 1 value of 0 to 7 and a C8 to C18 fatty acid as the second acid.

19 Claims, 2 Drawing Sheets

FILTER MEDIUM FOR DEACTIVATING ALLERGENS

CROSS-REFERENCE TO RELATED APPLICATIONS

Figure 1:
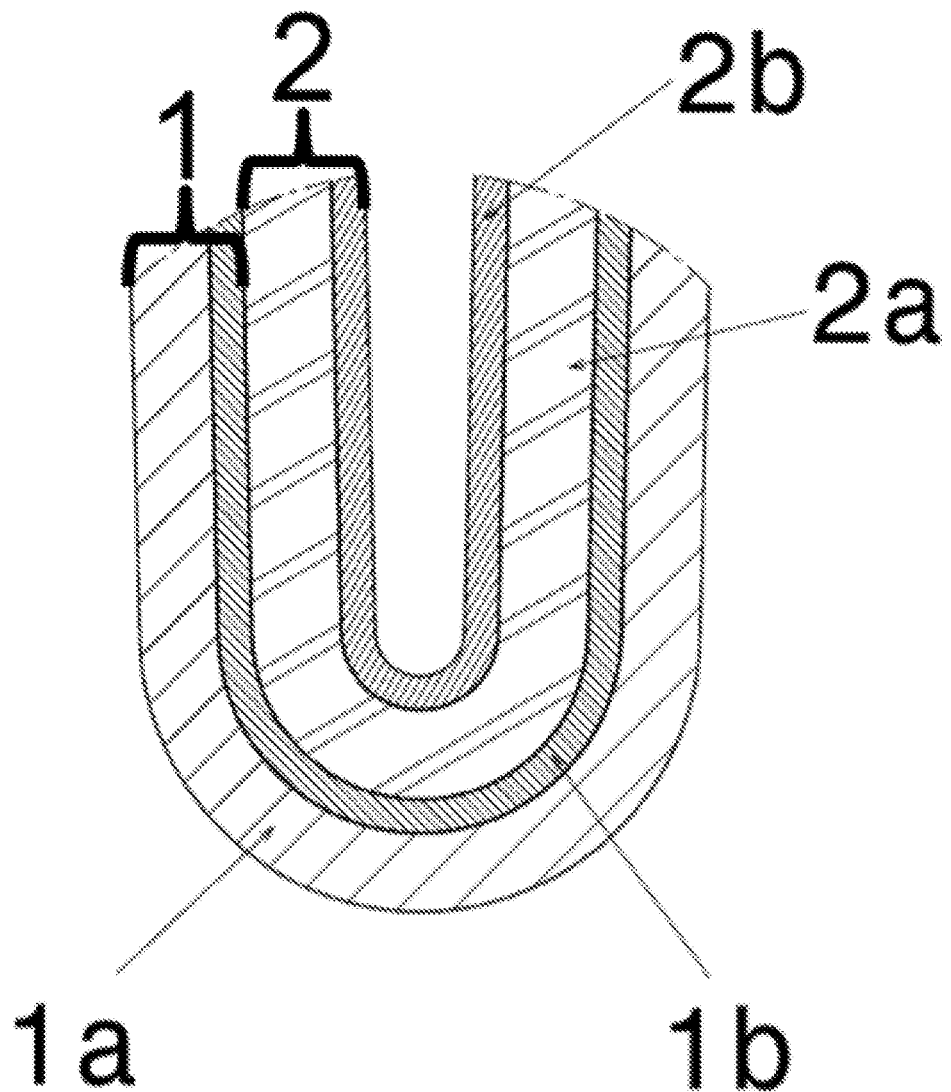

Priority is claimed to European Patent Application No. EP 15 192 601.1, filed on Nov. 2, 2015, the entire disclosure of which is hereby incorporated by reference herein.

FIELD

The invention relates to a filter medium, particularly for filtering gas particle systems, and to a filter arrangement comprising the filter medium.

BACKGROUND

Allergens are substances which trigger hypersensitivity reactions via the immune system. Statistics show that the number of people affected by such hypersensitivity reactions, triggered by allergens, is rising year by year. A large number of allergens, for example pollen, are transported by air, which is a problem particularly for asthmatics who react particularly sensitively to these allergens. Moreover, the number of asthmatics is increasing annually, which also exacerbates the situation.

Thus, there is a rising demand for filter materials which can remove the allergens from the air and can preferably also neutralize them.

In practice, polyphenols are often considered for reducing the allergy-triggering potential of the substances deposited on filter media, particularly tree pollen or house dust mite excrement. Thus, EP2879776 (A1) discloses the use of an allergen deactivator, comprising inter alia polyphenols from the family of tannins, in particular organic tannic acids in a filter medium. However, a disadvantage of polyphenols is that they have a relatively low anti-allergic potential, for example on filters, over a relatively long period of time: polyphenols as secondary plant substances mainly have a hydrophilic character and can therefore be degraded or washed out by ageing processes (large fluctuations in temperature and humidity) over the period of use of the filter.

US 2013/0183879 A1 describes the use of an allergen deactivator, comprising an aromatic sulphonic acid derivative in a filter medium. Organic acids are mentioned as auxiliaries. Aromatic sulphonic acid derivatives generally have an antibacterial action. However, a disadvantage of these substances is that resistances can develop.

SUMMARY

An aspect of the invention provides a filter medium, comprising: an acid-functionalized layer, wherein the acid-functionalized layer comprises a first acid with a $pK_{a1}$ value of 0 to 7 and a second acid comprising a C8 to C18 fatty acid.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following:

FIG. 1 shows a filter arrangement according to the invention with an absorbing region 1 and a particle-filtering region 2, the particle-filtering region 2 comprising a particle filter carrier layer 1*a* impregnated with lauric acid and citric acid; and FIG. 2 shows a further filter arrangement according to the invention with an absorbing region 1 and a particle-filtering region 2, the particle-filtering region 2 comprising a cover layer 1*c* impregnated with lauric acid and citric acid.

DETAILED DESCRIPTION

An aspect of the invention is to provide a filter medium which at least partly solves the above-mentioned problems and can effectively remove allergens from the air and neutralize them over a long period of time, for example over the period of use of the filter. Furthermore, the filter medium should have a bactericidal action and, as a result, should remain hygienic and odorless for a long period of time. An aspect of the invention provides a filter medium, particularly for filtering gas particle systems, and a filter arrangement comprising the filter medium. An aspect of the invention involves the use of the filter medium for producing supply air filters for buildings, car interior supply air filters and/or room air filters. The filter medium and the filter arrangement are outstandingly suitable for deactivating allergens.

An aspect of the invention is achieved by a filter medium, in particular by a medium for filtering gas particle systems, comprising at least one acid-functionalized layer which has a first acid with a pks1 value of 0 to 7, preferably from 1 to 5, more preferably from 2 to 4 and in particular from 2.5 to 3.5, as well as a C8 to C18 fatty acid as the second acid.

According to an aspect of the invention, it has been found that the combination of an acid having a pks1 value of 0 to 7 and C8 to C18 fatty acids makes it possible to provide filter media with a high capacity for deactivating allergens. This was surprising, as it was assumed that due to their oily nature, fatty acids would block the activity of the anti-allergenic acids. In fact, in practical tests, a reduction of the deactivation activity of these acids applied to filter media was found, but to a significantly smaller extent than was assumed. Without wishing to be committed to a mechanism according to the invention, it is assumed that the two classes of acid act synergistically such that the fatty acids as oily substances improve the separation and fixing of the allergens on the filter medium, as a result of which the blocking of the anti-allergenic acids is at least partly compensated.

Furthermore, it has been found that the deactivation of allergens can last for a surprisingly long period of time. Thus, it has been demonstrated in practical (simulation) tests that the addition of C8 to C18 fatty acids can decrease a reduction in the allergen deactivation activity, which reduction occurs due to simulated ageing processes (for example large fluctuations in temperature and humidity), by washing out the first anti-allergenically active acid.

Furthermore, it has surprisingly been found that the first acids which are used according to the invention have a high availability in the filter medium even after a drying procedure. This is a great advantage compared to polyphenols, the allergen deactivation activity of which can be lost to some extent during drying processes during production of the filter medium.

As the first acid, it is possible to select all kinds of acids which have a pks1 value of 0 to 7, preferably from 1 to 5, more preferably from 2 to 4 and in particular from 2.5 to 3.5. In this respect, the pks value can be determined by acid-base titration.

According to a preferred embodiment of the invention, the first acid is an acid soluble in water to very soluble in water. This can ensure a high availability of the active component.

The first acid is advantageously applied in aqueous or alcoholic solution to the layer to be functionalized. This is a particularly simple procedure.

Fruit acids, preferably malic acid, fumaric acid, gluconic acid, glycolic acid, mandelic acid, lactic acid, oxalic acid, salicylic acid, α-hydroxycaprylic acid, tartaric acid, citric acid and mixtures thereof have proved to be particularly suitable. The use of citric acid is particularly preferred according to the invention.

In principle, it is conceivable for the first acid and the second acid to be the same compounds. However, according to the invention it is preferred that they are different compounds.

According to the invention, all kinds of fatty acids or mixtures thereof can be used as the second acid. Fatty acids are aliphatic monocarboxylic acids with, in most cases, an unbranched carbon chain. According to the invention, fatty acids, selected from the group consisting of C8 to C18 fatty acids, C8 to C16 fatty acids, C12 to C14 fatty acids, C8, C10, C12 fatty acids and mixtures thereof have proved to be particularly suitable. The fatty acids preferably have an unbranched carbon chain. The fatty acids can be saturated or unsaturated or can comprise mixtures of saturated and unsaturated fatty acids. Saturated fatty acids and/or unsaturated fatty acids having 1 to 5 double bonds are preferred according to the invention.

The use of caprylic acid, pelargonic acid, capric acid, undecanoic acid, lauric acid, tridecanoic acid, myristic acid, pentadecanoic acid, palmitic acid and/or mixtures thereof have proved to be particularly effective as the second acid.

Also suitable are fatty acid derivatives, in particular fatty acids which contain hydroxy groups as functional radicals, as well as fatty acid esters, fatty acid amines, in particular oleic acid amides and stearic acid amides and/or mixtures thereof.

The molecules of the most frequent fatty acids have 16 or 18 carbon atoms. These are therefore particularly economical. In addition, the sodium and potassium salts of these fatty acids have the advantage of acting as surfactants.

C8 to C18 fatty acids which are slightly soluble to practically insoluble in water are particularly suitable according to the invention as the second acid.

Lauric acid is preferred according to the invention. Lauric acid is a very mild antimicrobial substance and consequently is not subject to any strict regulations during use. Nevertheless, lauric acid in the filter medium according to the invention exhibits a very satisfactory biocidal effect.

The combination of lauric acid and citric acid is particularly preferred according to the invention. It could be confirmed in practical tests that this combination can provide a filter medium with an outstanding anti-allergenic and anti-microbial effect for a long period of time, preferably over the entire period of use of a filter. In addition, both compounds exhibit a good environmental compatibility and do not make any extreme demands on worker safety during the processing thereof.

The ratio between the first acid and the second acid in the acid-functionalized layer can be adjusted subject to the desired performance of the filter medium. In particular, ratios ranging from 10,000:1 to 1:1, preferably from 1000:1 to 2:1, more preferably 100:1 to 5:1 have proved to be suitable.

The proportion of the first acid and of the second acid in the acid-functionalized layer can also be adjusted subject to the desired performance of the filter medium. It has proved to be particularly suitable to set the proportion of the first acid in the acid-functionalized layer at 0.1 wt. % to 30 wt. %, preferably from 2 wt. % to 24 wt. %, more preferably from 6 wt. % to 18 wt. %, more preferably from 7 wt. % to 15 wt. % and in particular from 8 wt. % to 12 wt. %, and/or to set the proportion of the second acid in the acid-functionalized layer at less than 10 wt. %, preferably from 0.01 wt. % to 5 wt. %, more preferably from 0.02 wt. % to 1 wt. %, more preferably from 0.04 wt. % to 0.6 wt. % and in particular from 0.08 wt. % to 0.12 wt. %, in each case based on the weight of the acid-functionalized layer. It has been found that when the concentration of fatty acid is increased, the anti-allergenic activity of the first acid is reduced by too great an extent.

It has also been found in practical tests that a filter medium according to the invention already having a relatively small proportion of fatty acid exhibits an outstanding deactivation of allergenic substances combined with a biocidal action.

The layer to be functionalized can be provided with the first and the second acid in different ways known to a person skilled in the art, such as by impregnation and/or coating, for example by slop padding, padding, spraying and/or dipping. The layer to be functionalized can thus easily be impregnated and/or coated with a solution and/or suspension containing the first and the second acid. It is also conceivable to impregnate and/or to coat the layer with a binder mixture, for example a thermoplastic binder, which contains the first and second acids.

Non-woven fabrics, woven fabrics, knitted fabrics and/or papers can preferably be used as carrier materials for the acid-functionalized layer. Thus, an embodiment which is particularly preferred according to the invention comprises the formation of the acid-functionalized layer as an impregnated and/or coated non-woven fabric, as an impregnated and/or coated woven fabric, knitted fabric and/or paper. In this respect, the use of a non-woven fabric is particularly preferred according to the invention.

In a particularly preferred embodiment of the invention, during the production of the filter medium, the layer to be functionalized is treated with a surface-active substance as wetting agent, preferably with one or more non-ionic surfactants as wetting agent, more preferably with ethoxylated sorbitane fatty acid esters (polysorbates) before and/or at the same time as the application of the second acid. Polysorbates are particularly preferred which are authorized as a food additive in the European Union based on REGULATION (EG) No. 1333/2008 OF THE EUROPEAN PARLIAMENT AND COUNCIL of 16 Dec. 2008, for example E432, E434, E435 and E436. Also preferred are polysorbates which are used in the pharmaceutical industry for virus inactivation, such as polysorbate 80 (E433). This measure can provide the filter medium with a further functionality. An advantage of the use of wetting agents is that the first and/or second acid can be anchored particularly effectively on the layer to be functionalized. This allows a good immobilization and deactivation of the allergens. With regard to the use of odor-intensive active ingredients, the surface-active substance affords the additional advantage that the release of odor can also be reduced due to the immobilization of these substances.

The filter medium can also contain further allergen-eliminating compounds, such as polyphenols, in particular flavonoids, phenolic acids, polyhydroxyphenols, anthocyanins, procyanidins, benzoic acid derivatives and stilbene derivatives, preferably of a natural origin, such as the plant secondary substances found in pomegranate, ginko or grape seed flour and/or mixtures thereof. In this respect, these compounds are preferably present in a quantity of 2% to 20%, in each case based on the total weight of the filter medium.

The filter medium can also contain fungicidal active ingredients. For this purpose, the acid-functionalized layer can be treated with a fungicidal substance, preferably with triazoles such as in particular 2-octyl 2H isothiazol-3-one and/or metals and the compounds thereof, for example zinc pyrethiones, before and/or at the same time as the application of the fatty acid.

The filter medium can be present in one or multiple layers. The filter medium according to the invention is outstandingly suitable for the production of filters, in particular for supply air filters for buildings, car interior supply air filters and/or room air filters.

A further subject of the present invention is a filter arrangement comprising a filter medium, as described above. In a preferred embodiment of the invention, the filter arrangement has a particle-filtering region and/or an absorbing region, it being possible for the filter medium to be comprised of one or both of these regions.

In a particularly preferred embodiment of the invention, the filter arrangement has the following components:

(A) a particle-filtering region, comprising
a particle filter carrier layer, and
a microfiber layer and/or a membrane filter layer arranged on the particle filter carrier layer,
optionally a cover layer arranged on the side of the microfiber layer and/or membrane filter layer remote from the particle filter carrier layer; and/or
(B) an absorbing region, comprising
an adsorption layer, and
an adsorption carrier layer arranged on the adsorption layer, at least one layer selected from particle filter carrier layer, microfiber layer, membrane filter layer, cover layer, adsorption layer and adsorption carrier layer being formed from a filter medium as described above.

According to the invention, "particle filter carrier layer" is understood as meaning a layer which can be used as a carrier layer for a microfiber layer and/or for a membrane filter layer.

According to the invention, "membrane filter layer" is understood as meaning a layer which is a permeable membrane.

According to the invention, "cover layer" is understood as meaning a layer which can be used for covering and protecting the microfiber layer and/or the membrane filter layer.

According to the invention, "adsorption layer" is understood as meaning a layer which has an adsorbent. This is preferably selected from the group consisting of activated carbon particles, zeolites, ion exchangers and mixtures thereof. The adsorbent is advantageously arranged in the adsorption layer in a statistically irregular manner as a flow-through packed bed on the adsorption carrier layer.

According to the invention, "adsorption carrier layer" is understood as meaning a layer which can be used as a carrier layer for the adsorption layer.

The adsorbing region of the filter medium can also consist of a geometrically determined arrangement of the adsorbent, for example as a flow-through honeycomb body of a defined cell shape and/or the use of a geometrically defined carrier structure for mechanically stabilizing an adsorption layer.

It is conceivable for the filter arrangement to comprise only the particle-filtering region or the absorbing region. However, the filter arrangement advantageously comprises both the particle-filtering region and the absorbing region, as this provides a particularly effective filter arrangement. In this case, the two regions are preferably arranged so that the adsorption layer is arranged on the side of the microfiber layer, the membrane filter layer or the cover layer which is remote from the particle filter carrier layer. Furthermore, during use, the filter arrangement is preferably arranged so that the particle-filtering region is upstream of the absorbing region in respect of the direction of flow. As a result, active ingredients which are present in the absorbing region, for example the first and second acid, can be protected before being covered with foreign particles from the supply air.

According to the invention, at least one layer, selected from particle filter carrier layer, microfiber layer, membrane filter layer, cover layer, adsorption layer and adsorption carrier layer, is formed from a filter medium as described above and thus has the combination according to the invention of the first and second acid. The specific embodiments described above of the filter medium can be carried over to the respectively corresponding layers of the filter arrangement. In principle, just a single layer or also different layers of the filter arrangement can have the combination according to the invention of the first and second acid.

An advantage of introducing the first and second acid into the particle filter carrier layer is that said layer usually faces the air flow as the first layer of the filter arrangement and thus allergen-containing particles and dust in the air flow can be deactivated before penetrating into the lower-lying layers of the filter arrangement.

In a preferred embodiment of the invention, the first and the second acid are contained in the cover layer. An advantage of this embodiment is that the upstream layers in the filter arrangement are not influenced in respect of their filtering characteristics. Furthermore, the first and the second acid can also be protected here before being covered with foreign particles from the supply air. This arrangement can be even more advantageous if the first and the second acid are not present in the particle filter carrier layer, or in the microfiber layer or in the membrane filter layer.

An advantage of introducing the first and second acid into the adsorption layer is that adsorption layers generally provide high specific surfaces (when activated carbon is used, approximately 1000 $m^2/g$) and therefore a large reactive surface is available for the allergen deactivation. Furthermore, here as well, the first and the second acid can be protected by the particle-filtering region or by the adsorption carrier layer before being covered with foreign particles from the supply air.

An advantage of introducing the first and second acid into the adsorption carrier layer is that the upstream layers in the filter arrangement are not influenced in respect of their filtering characteristics by the introduction of the first and second acid into the adsorption carrier layer. Furthermore, the first and second acid can be protected by the particle-filtering region before being covered with foreign particles from the supply air.

In an embodiment which is particularly preferred according to the invention, the filter arrangement is constructed as follows in respect of the direction of flow: particle filter carrier layer, microfiber layer, adsorption layer and adsorption carrier layer. In this respect, during use, the particle filter carrier layer is advantageously arranged on the onflow side.

As stated above, the carrier materials for the particle filter carrier layer, the microfiber layer, the membrane filter layer, the cover layer and the adsorption carrier layer can advantageously be non-woven fabrics, woven fabrics, knitted fabrics and/or papers.

It has also proved to be suitable to set the proportion of the first acid in the filter arrangement at 0.003 wt. % to 30 wt. %, preferably from 0.1 wt. % to 24 wt. %, more preferably from 0.2 wt. % to 18 wt. %, more preferably from 0.25 wt. % to 15 wt. % and in particular from 0.3 wt. % to 12 wt. %, and/or to set the proportion of the second acid in the filter arrangement at 0.0001 wt. % to 10 wt. %, more preferably from 0.0003 wt. % to 5 wt. %, more preferably from 0.0006 wt. % to 1 wt. %, more preferably from 0.001 wt. % to 0.6 wt. % and in particular from 0.003 wt. % to 0.12 wt. %, in each case based on the total weight of the filter arrangement.

In a preferred embodiment of the invention, the adsorption carrier layer and/or the particle filter layer has a non-woven fabric, preferably selected from spunbonded non-wovens, having an average fiber diameter within a range of 20 to 70 µm, preferably from 20 to 50 µm, in particular from 20 to 50 µm and/or staple fiber non-wovens having an average fiber diameter of 5 to 60 µm, preferably from 10 to 50 µm, in particular from 10 to 35 µm and/or an average fiber length of 10 to 100 mm, preferably 30 to 80 mm. Also advantageously, the microfiber layer and/or the membrane filter layer has a non-woven fabric, preferably selected from melt-blown non-wovens having an average fiber diameter of 1 µm to 10 µm. Also advantageously, the cover layer has a non-woven fabric, preferably selected from spunbonded non-wovens, having an average fiber diameter within a range of 20 to 60 µm and/or staple fiber non-wovens having an average fiber diameter of 10 to 50 µm.

An embodiment which is particularly preferred according to the invention comprises forming the adsorption carrier layer, the particle filter carrier layer, the microfiber layer, the membrane filter layer and/or the cover layer as non-woven fabric impregnated and/or coated with the first and second acid, as described above.

The filter medium according to the invention and the filter arrangement are outstandingly suitable for filtering supply air of buildings, car interior supply air and/or room air and, in this respect, particularly for filtering car interior supply air.

FIG. 1 shows a filter arrangement according to the invention comprising a particle-filtering region 1, which has
(A) a particle filter carrier layer 1a, and
a microfiber layer 1b, arranged on the particle filter carrier layer 1a, and
(B) an absorbing region 2, comprising
an adsorption layer 2a, arranged on the side of the microfiber layer 1b remote from the particle filter carrier layer 1a, and
an adsorption carrier layer 2b arranged on the side of the adsorption layer 2a remote from the microfiber layer 1b.

In this embodiment, the particle filter carrier layer 1a is formed as non-woven fabric impregnated with lauric acid and citric acid.

Figure 2:
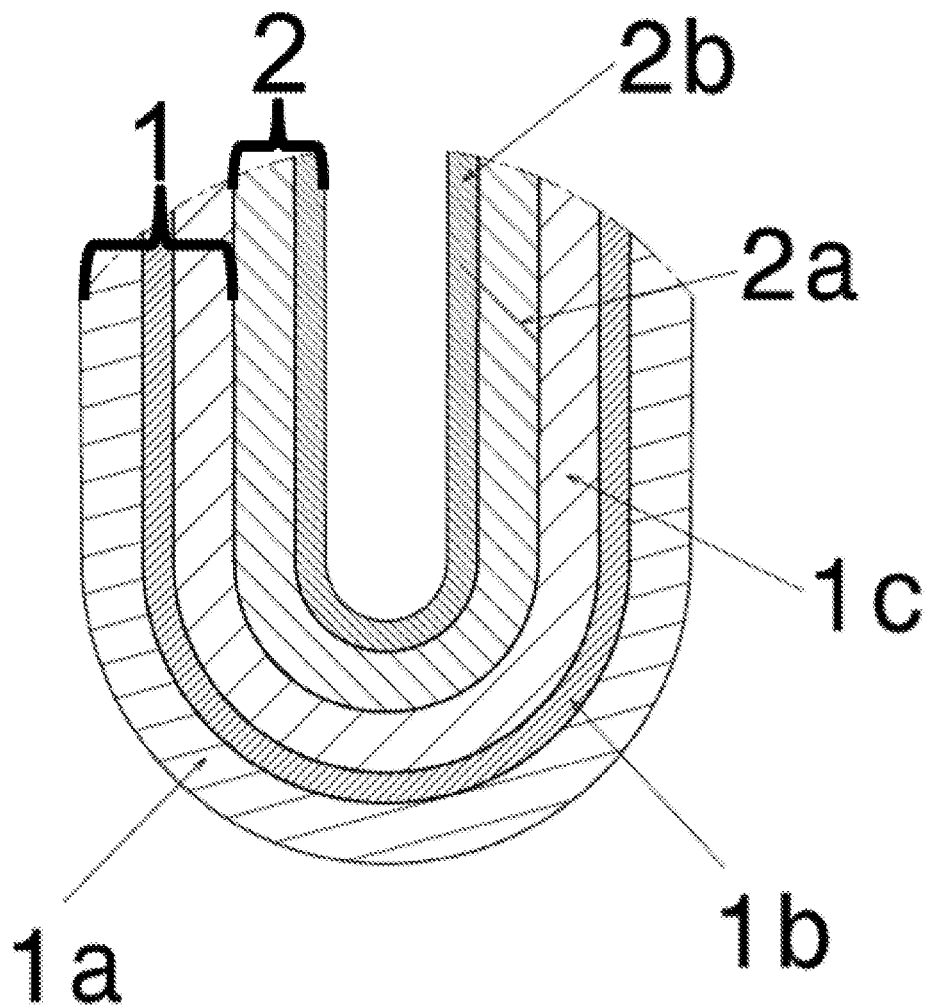

FIG. 2 shows a filter arrangement according to the invention comprising a particle-filtering region 1, which has
(A) a particle filter carrier layer 1a, and
a microfiber layer 1b, arranged on the particle filter carrier layer 1a,
and a cover layer (1c) arranged on the side of the microfiber layer 1b remote from the particle filter carrier layer 1a; and
(B) an absorbing region 2, comprising
an adsorption layer 2a arranged on the side of the cover layer (1c) remote from the microfiber layer 1b, and
an adsorption carrier layer 2b arranged on the side of the adsorption layer 2a remote from the cover layer (1c).

In this embodiment, the adsorption carrier layer 2b is formed as non-woven fabric impregnated with lauric acid and citric acid.

Measuring Methods:
Measuring the pks Values
The pks values in the present invention can be determined by evaluating the titration curves obtained by acid-base titration (Daniel C. Harris, Lehrbuch der quantitativen Analyse, Springer Verlag 2014).

Classification of the Water Solubility of the Acids
The water solubility in the present invention is verbally classified in accordance with the European Pharmacopoeia (8th Edition, 3rd Appendix, official German edition).

| Verbal classification of water solubility | Water solubility of substance in g/l |
|---|---|
| very soluble | >1000 |
| freely soluble | 100 to 1000 |
| soluble | 33 to 100 |
| sparingly soluble | 10 to 33 |
| slightly soluble | 1 to 10 |
| very slightly soluble | 0.1 to 1 |
| practically insoluble | <0.1 |

The solubility was measured in accordance with REGULATION (EG) No. 440/2008 OF THE COMMISSION of 30 May 2008 for establishing test methods according to Regulation (EG) No. 1907/2006 of the European Parliament and of the Council for the Registration, Evaluation, Authorization and Restriction of Chemicals (REACH).
Part A: Methods for Determining the Physico-Chemical Characteristics
A.6. Water Solubility
Preliminary Experiment Approximately 0.1 g of the sample (solid substances must be pulverized) are introduced into a 10 ml measuring cylinder which can be closed by a glass stopper. According to the table, distilled water at room temperature is added in portions.

| | ml water into 0.1 g soluble substance | | | | | | |
|---|---|---|---|---|---|---|---|
| | 0.1 | 0.5 | 1 | 2 | 10 | 100 | >100 |
| Approximate solubility in water (g/l) | >1000 | 1000-2000 | 200-100 | 100-50 | 50-10 | 10-1 | <1 |

After each addition of the quantity of water stated in the table, the mixture is shaken vigorously for 10 minutes and examined visually for undissolved particles. If after the addition of 10 ml of water, the sample or parts thereof are still undissolved, the experiment is to be repeated in a 100 ml measuring cylinder with greater quantities of water. In the case of low water solubility, the time required for a substance to dissolve can be considerably longer (up to 24 hours). The approximate water solubility is stated in the table, more specifically under the volume of water required for completely dissolving the sample. If the substance still has not completely dissolved, the experiment should be carried out for more than 24 hours (maximum 96 hours), or it should be further diluted to establish whether the column elution method or the shake flask method should be used.

The two test methods (described in the following) cover the entire range of water solubilities, but are not suitable for volatile substances:

a test method for substantially pure substances of a low water solubility ($<10^{-2}$ g/l), which are stable in water; this method is known as the "column elution method".

the other test method is suitable for substantially pure substances of a higher water solubility ($>10^{-2}$ g/l), which are stable in water; this method is known as the "shake flask method".

Description of the Method:
Test Conditions

The test is preferably carried out at 20° C.±0.5° C. If there appears to be a temperature dependence of the water solubility of >3%/° C., measurements are also carried out at two further temperatures which are at least 10° C. below and above the originally chosen temperature. In this case, the temperature stability should be ±0.1° C. The chosen temperature should be kept constant in the important parts of the apparatus.

EXAMPLES

In the following, the invention will be described in detail on the basis of several non-restrictive examples.

In the examples, ELISA (enzyme-linked immunosorbent assay) is used as a method for measuring the deactivation abilities of different active ingredient compositions in respect of particular allergens.

The ELISA method can measure allergen concentrations by assessing color changes due to antigen-antibody reactions.

Each example is based on tests using the active ingredients mentioned according to the invention in different weight proportions for specific allergens.

1. Sample Preparation

A carrier non-woven fabric of polyester spunbonded non-woven (weight per unit area 125 g/m²) is finished in an allergen-deactivating manner with a mixture of lauric acid and citric acid. The allergen-deactivating doping of the carrier non-woven is carried out by applying a mixture of the active ingredients in aqueous solution to the carrier non-woven and subsequently drying the now finished non-woven fabric to thereby obtain a sample for analysis.

The size of the sample used in the test is 10 mm×10 mm.

1.1 Preparation of the Antigen-Containing Starting Solution

Allergen sources used and antigens to be tested:
a) Allergen house dust mite: Antigen Der p1 from excrement
b) Allergen birch pollen: Antigen Bet v1 from pollen Allergen sources from Allergon AB, Ängelholm, Sweden were used. To prepare a test allergen solution of a defined starting concentration, each allergen source is dissolved in PBS buffer solution according to the specifications of the ELISA kit manufacturer, Indoor Biotechnologies Inc., Charlottesville, USA, to thereby produce a test allergen solution having a defined starting antigen content. Other reagents are used according to the specifications of the ELISA kit manufacturer.

1.2 Testing the Filter Medium for the Allergen-Deactivating Efficiency Thereof

Each sample, cut into 10 mm×10 mm pieces, is soaked at 25° C. for 1 hour in 300 μl of the allergen solution of a known starting antigen concentration.

An ELISA test kit is used for each antigen.

After soaking for one hour, 100 μl of the solution (supernatant) are pipetted into a 96-well microplate coated with antibodies.

The absorption of the microplate is established according to the specifications of the ELISA kit manufacturer using a microplate reading device at a wavelength of 405 nm and thus the allergen concentration (antigen content) of each sample is determined.

1.3 Measurement of the Test Results

To determine the allergen-deactivating efficiency, each antigen concentration of the sample reaction solution is determined according to the specifications of the ELISA kit manufacturer using a microplate reading device at a wavelength of 405 nm.

$$\text{Efficiency (\%)} = \frac{\text{starting concentration} - \text{measured allergen concentration of sample}}{\text{starting concentration}}$$

Here, the starting concentration and the measured allergen concentration of the sample correspond to an antigen-specific concentration in ng/ml.

2. Testing the Immunological Effect of Fruit Acids Subject to Type and Concentration The efficiency of the allergen elimination (birch allergen; Bet v1) of different fruit acids was tested. The starting concentration corresponds to the addition of 303 ng/ml Antigen Bet v1.

First of all, a carrier non-woven fabric of polyester spunbonded non-woven (weight per unit area 125 g/m²) was finished in an allergen-deactivating manner with citric acid or malic acid of different concentrations. As a result, obtained as material 1 was a filter medium, finished with 10 wt. % citric acid, obtained as material 3 was a filter medium finished with 1 wt. % citric acid, obtained as material 4 was a filter medium finished with 10 wt. % malic acid, and obtained as material 5 was a filter medium finished with 1 wt. % malic acid.

The result is shown in the following table:

TABLE 1

| Material | Addition of antigen | Efficiency |
|---|---|---|
| Material 1 | 303 ng/ml Bet v1 | 81% |
| Material 3 | 303 ng/ml Bet v1 | 10% |
| Material 4 | 303 ng/ml Bet v1 | 83% |
| Material 5 | 303 ng/ml Bet v1 | 15% |

It is found that citric acid and malic acid have a high allergen-eliminating effect, which increases with increasing concentration. It is surprising that the acids are active even in a dry state, which demonstrates the high stability of the acids.

3. ELISA Test: Fruit Acids Combined with Fatty Acids and Further Allergen-Eliminating Substances The efficiency of the allergen elimination (mite excrement allergen; Antigen Der p1) of different fruit acids combined with fatty acids was tested. The starting concentration corresponds to the addition of 232 ng/ml Antigen Der p1.

First of all, a carrier non-woven fabric of polyester spunbonded non-woven (weight per unit area 125 g/m²) was finished in an allergen-deactivating manner with citric acid, lauric acid, Tween 80 detergent and grape seed flour of different concentrations. As a result, obtained as material 6 was a filter medium finished with 5 wt. % citric acid, obtained as material 7 was a filter medium finished with 5 wt. % citric acid and 5 wt. % lauric acid, obtained as material 8 was a filter medium finished with 5 wt. % citric acid, 5 wt. % lauric acid and 0.5% Tween 80, and obtained as material 9 was a filter medium finished with 5 wt. % citric acid, 5 wt. % lauric acid, 0.5 wt. % Tween 80 and 10 wt. % grape seed flour.

The result is shown in Table 2.

TABLE 2

| Material | Addition of antigen | Efficiency |
| --- | --- | --- |
| Material 6 | 232 ng/ml Der p1 | 68% |
| Material 7 | 232 ng/ml Der p1 | 42% |
| Material 8 | 232 ng/ml Der p1 | 11% |
| Material 9 | 232 ng/ml Der p1 | 21% |

The results show that although the availability of the fruit acids is reduced due to the addition of fatty acid, a satisfactory efficiency is nevertheless retained. As expected, the addition of relatively high concentrations of Tween 80 detergent also reduces the availability of the fruit acids, but this does not result in complete inactivation.

The allergen-eliminating effect can be intensified by adding polyphenols, for example mixtures of flavonoids, phenolic acids, polyhydroxy phenols, anthocyanins, procyanidins as well as benzoic acid derivatives and stilbene derivatives, for example of a natural origin, such as grape seed flour.

4. ELISA Test: Optimization of the Active Ingredient Combinations

The efficiency of the allergen elimination (mite excrement allergen; Antigen Der p1) of optimized active ingredient combinations was tested. The starting concentration corresponds to an addition of 148 ng/ml Antigen Der p1.

As shown in FIG. 2, it is possible to obtain particularly good immunological effects of citric acid when the concentration thereof amounts to more than 5 wt. %, here 10 wt. %. It is also advantageous when lauric acid is in a quantity of less than 10 wt. %, preferably from 0.01 wt. % to 1 wt. %, in each case based on the weight of the acid-functionalized layer.

First of all, a carrier non-woven fabric of polyester spunbonded non-woven (weight per unit areal 25 g/m$^2$) was finished in an allergen-deactivating manner with citric acid, lauric acid and Tween 80 detergent in optimized concentration ratios. As a result, obtained as material 10 was a filter medium finished with 10 wt. % citric acid and 1 wt. % lauric acid, obtained as material 11 was a filter medium finished with 10 wt. % citric acid, 1 wt. % lauric acid and 0.5% Tween 80, and obtained as material 12 was a filter medium finished with 10 wt. % citric acid, 0.1 wt. % lauric acid and 0.5 wt. % Tween 80.

TABLE 3

| Material | Addition of antigen | Efficiency |
| --- | --- | --- |
| Material 10 | 148 ng/ml Der p1 | 91% |
| Material 11 | 148 ng/ml Der p1 | 90% |
| Material 12 | 148 ng/ml Der p1 | 91% |

5. ELISA Test (Comparison with Comparative Active Ingredient Potassium Carbonate)

The efficiency of the allergen elimination (mite excrement allergen; Antigen Der p1) of potassium carbonate as representative of basic anti-allergens was tested. The starting concentration corresponds to the addition of 140 ng/ml Antigen Der p1.

First of all, a carrier non-woven fabric of polyester spunbonded non-woven (weight per unit areal 25 g/m$^2$) was finished in an allergen-deactivating manner with potassium carbonate, lauric acid and Tween 80 detergent in defined concentration ratios.

As a result, obtained as material 13 was a filter medium finished with 5 wt. % potassium carbonate, obtained as material 14 was a filter medium finished with 5 wt. % potassium carbonate, 0.1 wt. % lauric acid and 0.5% Tween 80, obtained as material 15 was a filter medium finished with 10 wt. % potassium carbonate, and obtained as material 16 was a filter medium finished with 10 wt. % potassium carbonate, 0.1 wt. % lauric acid and 0.5 wt. % Tween 80.

TABLE 4

| Material | Addition of antigen | Efficiency |
| --- | --- | --- |
| Material 13 | 140 ng/ml Der p1 | 15% |
| Material 14 | 140 ng/ml Der p1 | 20% |
| Material 15 | 140 ng/ml Der p1 | 24% |
| Material 16 | 140 ng/ml Der p1 | 36% |

As shown in Table 4, the immunological effect of potassium carbonate is significantly lower than that of the acids used according to the invention.

6. Microbial Test

The microbial test of a filter medium according to the invention is carried out as follows according to the transfer method in accordance with the standard of the International Standards Organization (ISO) 20743:2013 (Textiles—Determination of antibacterial activity of textile products). A suspension of defined strains of bacteria with a known cell concentration is spread out over an agar plate of a petri dish. The filter medium according to the invention is placed on the petri dish. To transfer the bacteria onto the filter medium, said medium is weighed down with a weight of 200 g for a period of 1 minute. Thereafter, the filter medium, charged thus with bacteria, is incubated for 5 minutes at 37° C. in order to determine the starting concentration of bacteria on the filter medium in colony-forming units. This batch was used as the zero point value. The remaining samples of the filter medium were then incubated at 37° C. for a defined period of time (18-24 h) to determine the microbial efficiency of the filter medium.

An antimicrobial effect of the filter medium is present when the bacterial concentration on the filter medium at the end of the incubation period is lower than the bacterial concentration on the comparative sample which is free of active ingredient (in each case measured in colony-forming units KBE/ml).

The efficiency is calculated using the reduction factor and was carried out according to the standard of the International Standards Organization (ISO) 22196:2011 (Measurement of antibacterial activity on plastics and other non-porous surfaces), since the treated samples had such a strong antibacterial action that an almost complete destruction was achieved even after a few minutes. Therefore, these samples could not meaningfully be used as zero samples according to ISO 20743. Since in practice a suitable untreated textile comparative sample is often not available, in this case a calculation according to textile standard ISO 20743 is not expedient.

Therefore, the calculation was carried out as in ISO 22196 by comparing with an untreated sample for the same incubation time and, in this respect, the reduction factor is calculated according to the following formula:

$$R=[\log(B/A)-\log(C/A)]=[\log(B/C)]$$

R: value of the antimicrobial activity
A: living bacterial count on the test pieces directly after inoculation
B: living bacterial count on the zero sample free from active ingredient
C: living bacterial count on the test piece containing active ingredient In the event of a complete elimination of the bacteria on the test sample, the reduction factor cannot be calculated according to the above formula (indeterminacy due to division by 0). However, according to standard 22196, this problem does not arise, as while carrying out this method, a detection limit of 40 bacteria is provided in this case (since a 0.5 ml aliquot of the 20 ml rinsing solution is incubated and not the entire volume), and in this case, instead of 0, the detection limit of 40 is used in the above-mentioned formula.

The reduction factor is an indication of how many of the microorganisms which were contained in the original bacterial suspension and were directly applied to the finished material sample in the first step of the test die through contact with the biocidal material compared to the zero sample. Since the bacterial concentrations are stated as decimal powers, the calculation is made using the associated common logarithms.

Therefore, a reduction factor of 2 means that the concentration of bacterial suspension, after contact with the coated sample, is lower by 2 decimal powers compared to the zero sample. The greater the reduction factor, the greater the number of bacteria which die during contact with the finished surface and therefore the higher the efficiency of the coating/sample/etc.

The number of bacteria transferred onto the filter medium is quantified here by Koch's pour plate method.

The measurements were carried out in accordance with the standard ISO 20743. This standard can be applied to all textile products and materials for clothing, bed linen, household textiles and various goods, regardless of the type of antibacterial active ingredients which are used. Differing from this standard, the investigations were not carried out using the gram-negative reference germ *Klebsiella pneumoniae*, but using the likewise gram-negative germ *Escherichia coli*.

The *Escherichia coli* species does not usually cause illness, but there are numerous different pathogenic strains which belong to the most frequent causal agents of human infectious diseases. Furthermore, in Japanese standard JIS L1902 (Testing for antibacterial activity and efficacy on textile products), on the basis of which standard ISO 20743 was adopted, the germ *Escherichia coli* is named as a reference germ which is to be used. The reason why *Escherichia coli* is not used as the reference germ in all textile test standards for antibacterial activity is that it is extremely susceptible to drying out, which can be disruptive in the tests. This can be ruled out in the present case, because incubation was carried out at a relative air humidity of 90% and the germ count of the unfinished material sample increased over the incubation period (so-called blind value).

6.1 Microbial Test Using *Staphylococcus aureus* DSM 799 (Gram-Positive)

First of all, a carrier non-woven fabric of polyester spunbonded non-woven (weight per unit area 125 g/m$^2$) was finished in an allergen-deactivating manner with citric acid, lauric acid and Tween 80 detergent in optimized concentration ratios. As a result, obtained as material 11 was a filter medium finished with 10 wt. % citric acid, 1 wt. % lauric acid and 0.5% Tween 80, and obtained as material 12 was a filter medium finished with 10 wt. % citric acid, 0.1 wt. % lauric acid and 0.5 wt. % Tween 80. For comparison, the bacterial counts for the unfinished filter medium consisting of polyester spunbonded non-woven fabric (weight per unit area 125 g/m$^2$) were also determined (material 17).

In the following table, the biocidel effect of different filter media on the bacterium *Staphylococcus aureus* DSM 799 (gram-positive) after an incubation duration of 18 h is shown as a comparison.

TABLE 5

| Material | Reduction factor compared to untreated material (after 5 min exposure time) | Reduction factor compared to untreated material (after 18 h incubation) |
| --- | --- | --- |
| 11 | 3.7 | 6.7 |
| 12 | 3.3 | 6.7 |
| 17 | — | — |
| | (untreated material) | (untreated material) |

Table 5 shows that a biocidel effect can be achieved even with small contents of lauric acid of 0.1%. According to the invention, this effect increases as the quantity of lauric acid increases and/or when Tween 80 is used. In accordance with standard ISO 20743:2013, an antimicrobial effect of the filter medium is present for material 11 and material 12, since the common logarithmic reduction factor is >2.

6.2 Microbial Test Using *Escherichia coli* DSM 787 (Gram-Negative)

First of all, a carrier non-woven fabric of polyester spunbonded non-woven (weight per unit area 125 g/m$^2$) was finished in an allergen-deactivating manner with citric acid, lauric acid and Tween 80 detergent in optimized concentration ratios. As a result, obtained as material 11 was a filter medium finished with 10 wt. % citric acid, 1 wt. % lauric acid and 0.5% Tween 80, and obtained as material 12 was a filter medium finished with 10 wt. % citric acid, 0.1 wt. % lauric acid and 0.5 wt. % Tween 80. For comparison, the bacterial counts for the unfinished filter medium consisting of polyester spunbonded non-woven fabric (weight per unit area 125 g/m$^2$) were also determined (material 17).

In the following table, the biocidel effect of different filter media on the bacterium *Escherichia coli* DSM 787 (gram-negative) after an incubation duration of 22 h is shown as a comparison.

TABLE 6

| Material | Reduction factor compared to untreated material (after 5 min exposure time) | Reduction factor compared to untreated material (after 22 h incubation) |
| --- | --- | --- |
| 11 | 3.7 | 4.3 |
| 12 | 3.7 | 4.3 |
| 17 | — | — |
| | (untreated material) | (untreated material) |

Table 6 shows that a biocidel effect can be achieved even with small contents of lauric acid of 0.1%. According to standard ISO 20743:2013, an antimicrobial effect of the filter medium is present for material 11 and material 12, since the common logarithmic reduction factor is >2.

6.3 Adjustments of the Availability of the First Acid in Filter Media Over the Period of Use of the Filter A suitable measured variable for the availability of the first acid in filter media over the period of use of the filter is the determination of the pH of an aqueous solution in the samples of the filter medium finished with the first acid. Here, the pH of the aqueous solution was determined over several elution stages:

First of all, a carrier non-woven fabric of polyester spunbonded non-woven (weight per unit area 125 g/m$^2$) was finished in an allergen-deactivating manner exclusively with citric acid and furthermore with a mixture of citric acid and lauric acid. The allergen-deactivating doping was carried out here by applying a citric acid solution or a mixture of the active ingredients citric acid and lauric acid in aqueous solution to the filter medium and by subsequently drying the now finished non-woven fabric. As a result, obtained as material 1 was a filter medium finished with 10 wt. % citric acid, and obtained as material 2 was a filter medium finished with 10 wt. % citric acid and 5 wt. % lauric acid.

The question was whether lauric acid can slow down the release of citric acid and this would then be effective for a longer period of time. For this purpose, samples, 30 cm$^2$ in size, of the two differently finished filter media were introduced into a glass vial with 15 ml of ultrapure water with stirring by a magnetic stirrer for a period of 10 seconds, then removed from the vial and again introduced into a further new glass vial with the same volume of 15 ml of ultrapure water for the same period of 10 seconds. This approach was repeated several times. Thereafter, a pH meter determined the pH of each solution in order to establish a difference between material 1 and material 2 in their temporal release of citric acid. For this purpose, 30 cm$^2$ of the abovementioned filter media were tested, respectively in a triple determination, by means of the pH meter model Lab 860 of SI Analytics GmbH (55122 Mainz, Germany). Before the measurements, the pH meter (measurement range: pH: 2.000-19.999 (accuracy+/−0.005)) was calibrated by point calibration with two defined buffer solutions (pH=4 and pH=7.2). The pH is determined using a pH electrode model SI Analytics 285129147 BlueLine 14 pH electrode of SI Analytics GmbH (55122 Mainz, Germany). A temperature sensor is integrated into the above-mentioned pH electrode due to the temperature dependence of the pH determination. The measurements were carried out at 25° C. The measuring principle which is the basis for the determination of the pH using electrodes is potentiometry: a glass membrane ball, filled with buffer solution, is dipped into the liquid to be measured. Due to the tendency of the hydrogen ions to become attached in a thin layer to silicate groups of the glass surface, a galvanic voltage builds up between the inside and the outside of the ball, depending on the pH difference. This electromotive force is measured by two reference electrodes, one of which is located inside the glass ball and the other is in a reference electrolyte. In the case of the pH electrode described above, a silver/silver chloride (Ag/AgCl) reference system is used:

TABLE 7

| | pH value | | | | | |
|---|---|---|---|---|---|---|
| | Material 1 | | | Material 2 | | |
| Test | 1$^{st}$ test | 2$^{nd}$ test | 3$^{rd}$ test | 1$^{st}$ test | 2$^{nd}$ test | 3$^{rd}$ test |
| 1$^{st}$ glass vial | 3.9 | 3.9 | 3.9 | 4.1 | 4.0 | 4.0 |
| 2$^{nd}$ glass vial | 6.4 | 6.7 | 6.8 | 4.6 | 4.5 | 4.9 |
| 3$^{rd}$ glass vial | 7.0 | 7.0 | 7.0 | 5.8 | 5.9 | 6.0 |
| 4$^{th}$ glass vial | | | | 6.5 | 6.7 | 7.0 |
| 5$^{th}$ glass vial | | | | 7.0 | 7.0 | 7.0 |

As a result, it is found that the filter medium according to the invention only experiences a slight reduction in availability even under extreme conditions for gas filter media, i.e. when repeatedly dipped into water for a period of 10 seconds.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B, and C" should be interpreted as one or more of a group of elements consisting of A, B, and C, and should not be interpreted as requiring at least one of each of the listed elements A, B, and C, regardless of whether A, B, and C are related as categories or otherwise. Moreover, the recitation of "A, B, and/or C" or "at least one of A, B, or C" should be interpreted as including any singular entity from the listed elements, e.g., A, any subset from the listed elements, e.g., A and B, or the entire list of elements A, B, and C.

The invention claimed is:

1. A filter medium, comprising:
    an acid-functionalized layer,
    wherein the acid-functionalized layer comprises a first acid with a pK$_{a1}$ value of 0 to 7 and a second acid comprising a C8 to C18 fatty acid.

2. The medium of claim 1, wherein the first acid comprises a fruit acid.

3. The medium of claim 1, wherein the second acid comprises a C8 to C16 fatty acid.

4. The medium of claim 1, wherein the second acid is caprylic acid, pelargonic acid, capric acid, undecanoic acid, lauric acid, tridecanoic acid, myristic acid, pentadecanoic acid, palmitic acid, or a mixture thereof.

5. The medium of claim 1, wherein a ratio between the first acid and the second acid in the filter medium is in a range of from 10.000:1 to 1:1.

6. The medium of claim 1, wherein the acid-functionalized layer comprises the first acid in a quantity of 0.1 wt. % to 30 wt. %, and/or wherein the acid-functionalized layer comprises the second acid in a quantity of less than 10 wt. %, in each case based on the total weight of the acid-functionalized layer.

7. The medium of claim 1, wherein the acid-functionalized layer is an impregnated and/or coated non-woven fabric.

8. The medium of claim 1, wherein the acid-functionalized layer comprises a surface-active substance as wetting agent, applied before and/or at the same time as an application of the second acid.

9. The medium of claim 1, wherein the acid-functionalized layer comprises a fungicidal substance, applied before and/or at the same time as the application of the fatty acid.

10. A method of producing a supply air filter for a building, a car interior supply air filter, and/or room air filter, the method comprising contacting the medium of claim 1 with the filter.

11. A filter arrangement, comprising:
A) a particle-filtering region comprising (a1) a particle filter carrier layer, and (a2) a microfiber layer and/or membrane filter layer arranged on the particle filter carrier layer, and, optionally, (a3), a cover layer arranged on a side of the microfiber layer and/or membrane filter layer remote from the particle filter carrier layer; and/or
B) an absorbing region comprising (b1) an adsorption layer, and (b2) an adsorption carrier layer arranged on the adsorption layer (2a), wherein at least one of the particle filter carrier layer, microfiber layer, membrane filter layer, cover layer, adsorption layer, and adsorption carrier layer is formed from the medium of claim 1.

12. The arrangement of claim 11, wherein the adsorption layer comprises an adsorbent comprising an activated carbon particles, ion exchanger, zeolite, or a mixture of two or more of any of these.

13. The arrangement of claim 11, wherein the adsorption carrier layer and/or the particle filter layer comprises a non-woven fabric, comprising spunbonded non-wovens having an average fiber diameter within a range of 20 to 60 μm, and/or staple fiber non-wovens having an average fiber diameter of 10 to 50 μm, and/or wherein the microfiber layer and/or the membrane filter layer comprises a non-woven fabric, and/or wherein the cover layer comprises a non-woven fabric.

14. The medium of claim 1, configured to filtering gas particles.

15. The medium of claim 1, wherein the first acid comprises malic acid, fumaric acid, gluconic acid, glycolic acid, mandelic acid, lactic acid, oxalic acid, salicylic acid, α-hydroxycaprylic acid, tartaric acid, citric acid, or a mixture thereof.

16. The medium of claim 1, wherein the second acid comprises a C16 fatty acid, C12 to C14 fatty acids, C8, C10, C12 fatty acids and mixtures thereof.

17. The medium of claim 1, wherein the second acid comprises a C12 to C14 fatty acid.

18. The medium of claim 1, wherein the second acid comprises a C8 fatty acid, C10 fatty acid, C12 fatty acid, or a mixtures of two or more of any of these.

19. The medium of claim 1, wherein a ratio between the first acid and the second acid in the filter medium is in a range of from 100:1 to 5:1.

* * * * *